(12) United States Patent
Gottesburen et al.

(10) Patent No.: US 10,058,488 B2
(45) Date of Patent: Aug. 28, 2018

(54) SKIN CLEANSING ARTICLE IMPREGNATED WITH A LOW VOC CLEANER COMPRISING A 9-DECANOIC ACID METHYL ESTER

(71) Applicant: Illinois Tool Works Inc., Glenview, IL (US)

(72) Inventors: Paul J. Gottesburen, Olathe, KS (US); Lee R. Rieth, Olathe, KS (US)

(73) Assignee: Illinois Tool Works Inc., Glenview, IL (US)

( * ) Notice: Subject to any disclaimer, the term of this patent is extended or adjusted under 35 U.S.C. 154(b) by 7 days.

(21) Appl. No.: 15/286,389

(22) Filed: Oct. 5, 2016

(65) Prior Publication Data

US 2017/0105907 A1 Apr. 20, 2017

Related U.S. Application Data

(60) Provisional application No. 62/241,144, filed on Oct. 14, 2015.

(51) Int. Cl.

| | | |
|---|---|---|
| *A61K 8/37* | (2006.01) | |
| *A61K 8/31* | (2006.01) | |
| *A61Q 19/10* | (2006.01) | |
| *C11D 1/72* | (2006.01) | |
| *C11D 3/32* | (2006.01) | |
| *C11D 7/24* | (2006.01) | |
| *A61K 8/02* | (2006.01) | |
| *A61K 8/42* | (2006.01) | |
| *A61K 8/46* | (2006.01) | |
| *A61K 8/06* | (2006.01) | |
| *B65B 7/28* | (2006.01) | |
| *B65D 85/62* | (2006.01) | |
| *A61K 8/39* | (2006.01) | |

(52) U.S. Cl.
CPC ............ *A61K 8/0208* (2013.01); *A61K 8/068* (2013.01); *A61K 8/31* (2013.01); *A61K 8/37* (2013.01); *A61K 8/375* (2013.01); *A61K 8/39* (2013.01); *A61K 8/42* (2013.01); *A61K 8/466* (2013.01); *A61Q 19/10* (2013.01); *B65B 7/28* (2013.01); *B65D 85/62* (2013.01); *A61K 2800/28* (2013.01)

(58) Field of Classification Search
CPC ............ C11D 1/72; A61K 8/31; A61Q 19/10
See application file for complete search history.

(56) References Cited

U.S. PATENT DOCUMENTS

| | | | |
|---|---|---|---|
| 4,833,003 A | 5/1989 | Win et al. | |
| 5,523,025 A | 6/1996 | Erilli | |
| 5,683,971 A * | 11/1997 | Rose | ................ A47L 13/17 510/130 |
| 6,165,962 A | 12/2000 | Kaler et al. | |
| 8,809,255 B2 | 8/2014 | Plotz et al. | |
| 2013/0180066 A1* | 7/2013 | Plotz | ................ A61K 8/466 15/104.93 |
| 2015/0045278 A1 | 2/2015 | Beisser et al. | |
| 2017/0081621 A1* | 3/2017 | Hasinovic | ................ B08B 3/08 |

* cited by examiner

*Primary Examiner* — Charles Boyer
(74) *Attorney, Agent, or Firm* — Avery N. Goldstein; Blue Filament Law PLLC

(57) ABSTRACT

A hand cleaning article is provided that includes a towel presenting two opposing surfaces. A hand cleaning composition is impregnated into the towel and includes a first non-ionic surfactant that is a $C_{12}$-$C_{15}$ alkyl ethoxylated alcohol having an average degree of ethoxylation of from 3 to 7. A solvent is present of a dibasic ester microemulsion, $R^1$—$C(O)N(CH_3)_2$ where $R^1$ is a $C_2$-$C_{20}$ alkane, $C_3$-$C_{20}$ alkene, $C_6$-$C_{20}$ diene, or $R^2$—$C(O)O$—$(CH_2)_n$ where a $C_1$-$C_{20}$ alkane, $C_3$-$C_{20}$ alkene, or $C_6$-$C_{20}$ diene, and n is an integer of between 1 and 10, or a combination of the dibasic ester microemulsion and $R^1$—$C(O)N(CH_3)$. An organic co-solvent is provided of: a $C_4$-$C_{28}$ acid ester, $C_9$-$C_{16}$ hydrocarbons having a boiling in the range of 150° C. to 290° C., butyl 3-hydroxynutyrate, or a combination thereof. The majority of the composition is water.

20 Claims, No Drawings

SKIN CLEANSING ARTICLE IMPREGNATED WITH A LOW VOC CLEANER COMPRISING A 9-DECANOIC ACID METHYL ESTER

RELATED APPLICATIONS

This application claims priority benefit of U.S. Provisional Application Ser. No. 62/241,144 filed 14 Oct. 2015; the contents of which are hereby incorporated by reference.

FIELD OF THE INVENTION

The present invention in general relates to a cleaning composition for removal of lipophilic substances such as paints, resins, oils, and organic soils from skin and hard surfaces, and in particular to waterless cleaning composition for doing so with low VOC content.

BACKGROUND OF THE INVENTION

Waterless hand cleaners routinely have a gelatinous consistency. These cleaners often have both hydrophilic and hydrophobic components which are blended together to affect removal of a wide variety of soils from the skin surface. While the gelatinous hand cleaner is effective in removal of material from the skin surface, subsequent water washing is invariably required to remove the residual debris filled gel. Additionally, a gel independent of an abrasive is often slow in removing substance from the skin surface. Conventional waterless cleaning compositions often contain as much as 45% by weight of organic solvents and high loadings of emulsifiers in order to solubilize grease and soil. These compositions require high concentrations of organic solvents and emulsifiers to remove hydrophobic materials through dual actions of emulsification and solvation.

Low viscosity, liquid waterless hand cleaners have proven popular and effective when used in conjunction with an abrasive article that retains the liquid in contact with the skin surface and provides mechanical action to disrupt soil or grease films on the skin surface. Representative of such products are those detailed in U.S. Pat. No. 5,683,971 in which an abrasive coated towel retains the cleaning composition.

Regardless of the viscosity, these conventional cleaning compositions have fallen out of favor owing to the high loading of organic solvents and emulsifiers that end up in wastewater, as well as the skin irritation associated with the use of such products. Volatile organic compound content (VOC) in consumer products is now tightly regulated and the acceptable limits of VOCs in such products are constantly being lowered. The high concentration of organic solvents and emulsifiers present in these conventional cleaner also makes subsequent removal of the cleaner difficult, often resulting in a residual film that retains soil and/or grease while the film tends to dry and irritate the underlying dermis. Owing to the environmental impact, cost, and skin irritation caused by contact with cleaner residue, there is a desire to reduce the usage of such solvents without compromising the cleaning ability of such waterless hand cleaners.

A recent successful improved product relied upon the inclusion of a microemulsion to stabilize the low lipophilic content composition. This composition is detailed in U.S. Pat. No. 8,809,255. While highly effective, inks and asphaltic soils require effort to remove with low VOC compositions. Other low VOC microemulsions also have a limited cleaning spectrum compared to high VOC formulations, as detailed in US 2015/0045278.

Thus, there exists a need for a cleaning composition that is amenable to impregnation into an article that has reduced ecotoxicity and improved skin compatibility with still greater effectiveness against broad classes of inks, soils and greases.

SUMMARY OF THE INVENTION

A hand cleaning article is provided that includes a towel presenting two opposing surfaces. A hand cleaning composition is impregnated into the towel and includes 0.5 to 15 total weight percent of a first non-ionic surfactant that is a $C_{12}$-$C_{15}$ alkyl ethoxylated alcohol having an average degree of ethoxylation of from 3 to 7. 0.1 to 10 total weight percent of solvent of a dibasic ester microemulsion, $R^1$—C(O)N(CH$_3$)$_2$ where $R^1$ is a $C_2$-$C_{20}$ alkane, $C_3$-$C_{20}$ alkene, $C_6$-$C_{20}$ diene, or $R^2$—C(O)O—(CH$_2$)$_n$ where a $C_1$-$C_{20}$ alkane, $C_3$-$C_{20}$ alkene, or $C_6$-$C_{20}$ diene, and n is an integer of between 1 and 10, or a combination of the dibasic ester microemulsion and $R^1$—C(O)N(CH$_3$)$_2$ are also present in the composition. 0.1 to 15 total weight percent of an organic co-solvent of: a $C_4$-$C_{28}$ acid ester, $C_9$-$C_{16}$ hydrocarbons having a boiling in the range of 150° C. to 290° C., butyl 3-hydroxybutyrate, or a combination thereof are present, with the composition being a majority by weight water to impart better cleaning ability than a hand cleaner composition lacking any of the aforementioned components in the context of the hand cleaning article.

In certain inventive embodiments, the $C_4$-$C_{28}$ acid ester is 9-decanoic acid methyl ester. In other inventive embodiments, the $C_9$-$C_{16}$ hydrocarbons is present and includes catalytically hydrotreated hydrocarbons. A second non-ionic surfactant, an anionic surfactant, or a combination thereof are also present in certain inventive embodiments. In other inventive embodiments, at least one emollient is present in the composition. In still other inventive embodiments, the VOC is less than 2 total weight percent.

In still other inventive embodiments, the solvent is present from 1 to 4 total weight percent. Additives of a pH adjusting material, an antioxidant, a fragrance, a dye, a fungicide, or a foaming agent are readily provided to the composition. A polyvalent metal ion salt is added in some embodiments to an inventive composition.

An abrasive ingredient adhered to at least one of the two opposed surfaces to the towel produces physical abrasion when the towel is rubbed on a target debris. Towels can be provided in a continuous rolled cylinder, with each of the towels separated at a line of perforation. The towels can be stored in a selectively sealable, evaporation resistant container having a hollow interior in which the cylinder of towels are housed, the axis of said cylinder being coaxial with the container. A defines an opening in the container for receiving said plurality of said towels. The opening having a selectively closeable cap associated therewith.

A method for preparing a hand cleaning article is also provided that includes placing the continuous roll of towels into the container. The towels are then impregnated with the composition as detailed above. The lid of the container is then sealed to provide a moistened towel roll storage that inhibits water loss from the towels.

DETAILED DESCRIPTION OF THE PREFERRED EMBODIMENTS

The present invention has utility as a free flowing, liquid cleaning composition that is especially well-suited for removal of paint, resin, oils, and lipophilic soils from the skin surface with a low VOC content or no VOC content. The inventive cleaning composition is particularly well-suited as a hand cleaner for removing such substances and soils from a user's skin in combination with a towel, such as that detailed in U.S. Pat. No. 4,833,003. The inventive composition is impregnated into an article. Such wet articles are amenable to packaging in a container as a pre-perforated roll or stack of such articles that can be dispensed, used and discarded to affect cleaning without resorting to a secondary water washing or cleaner removal. The article in some embodiments has an abrasive ingredient associated with at least one surface of the article to provide mechanical forces to dislodge the target debris when the article is rubbed against the target debris. By reducing the VOC content of an inventive composition relative to the prior art, the environmental impact of the product is reduced along with the residual skin irritation.

It is to be understood that in instances where a range of values are provided, for example with respect to a weight percentage range of a composition component, that the range is intended to encompass not only the end point values of the range but also intermediate values of the range as explicitly being included within the range and varying by the last significant figure of the range. By way of example, a recited range of from 1 to 4 is intended to include 1-2, 1-3, 2-4, 3-4, and 1-4.

As used herein, a VOC is defined as a compound listed on the United States Environmental Protection Agency Volatile Organic Compounds Master List.

An inventive composition is able to replace in part or total regulatory controlled VOCs and still remain effective at removing lipophilic soils, greases, inks, and asphaltic soils through reliance on 0.5 to 15 total weight percent of a first non-ionic surfactant that is a $C_{12}$-$C_{15}$ alkyl ethoxylated alcohol having an average degree of ethoxylation of from 3 to 7 and 0.1 to 10 total weight percent of a dibasic ester microemulsion, 0.1 to 10 total weight percent of N,N-dimethyl 9-decenamide, or a combination thereof to replace in whole or part conventional waterless hand cleaner VOCs such as mineral spirits, limonene, and dibasic esters. The inventive composition also contains water as the majority be weight of the composition. In specific embodiments, the water is present from 60 to 99.7 total weight percent.

In contrast to the low VOC composition detailed in U.S. Pat. No. 8,809,255; the present invention uses 0.1 to 15 total weight percent of an organic co-solvent of: a $C_4$-$C_{28}$ acid ester, $C_9$-$C_{16}$ hydrocarbons having a boiling in the range of 150° C. to 290° C., butyl 3-hydroxybutyrate, or a combination thereof to promote removal of inks asphaltic soils, and silicone caulks in particular. It has been surprisingly found that amounts of from 0.1 to 1 total weight percent of such co-solvents are effective in increasing the ability of an article impregnated with such a composition to remove debris such as inks, asphaltic soils, and silicone caulks better than a microemulsion composition lacking such co-solvents.

In some inventive embodiments, inclusion of an additional surfactant of non-ionic or anionic type, or a combination thereof imparts additional surfactancy and cleaning ability to an inventive article. In some inventive embodiments the VOC content remains below 5 total weight percent and in still other embodiments below 1 total weight percent.

The present invention reduces VOC content, skin irritation, and has storage stability while maintaining conventional cleaning properties with respect to paints, resins, and other lipophilic soils and affording improved cleaning spectrum compared to other low VOC microemulsions such as those detailed in U.S. Pat. No. 8,809,255 and US 2015/0045278. Through selection of specific additives, antibacterial treatment is achieved and skin quality is also improved.

The formulary of an inventive cleaning composition is summarized below in Table 1.

TABLE 1

Inventive Cleaning Composition

| Component | Typical Amount Total Wt. Percent | Pref. Amount - Total Wt. Percent |
|---|---|---|
| Surfactant (non-ionic/anionic)* | 0.5-15 | 1-5 |
| Solvent: | | |
| (a) Microemulsion, or | 0.1-10 | 1-4 |
| (b) $R^1$—C(O)N(CH$_3$)$_2$, or | 0.1-10 | 1-4 |
| Combination (a) + (b) | 0.2-15 | 1-5 |
| Co-solvent | 0.1-15 | 1-4 |
| (a $C_4$-$C_{28}$ acid ester, $C_9$-$C_{16}$ hydrocarbons having a boiling in the range of 150° C. to 290° C., butyl 3-hydroxybutyrate, or a combination thereof) | | |
| Emollients | 0.1-10 | 1-6 |
| (alkylene glycol, glycerine, vitamin E acetate, dimethicone, lanolin, mineral oil, wheat germ extract, jojaba extract, etc., and combinations thereof) | | |
| Water | to 100% | to 100% |
| Optional components | | |
| Fragrance | 0-3 | 0.01-3 |
| Dye | 0-3 | 0.01-3 |
| pH adjustment additives (caustic, citric acid, etc.) | none -pH = 13 | 0 |
| Polyvalent metal ion salt | 0-2 | 0-2 |
| Antimicrobial | 0-2 | 0.005-1 |
| Foaming agent | 0-2 | 0-0.6 |
| Polar organic solvent | 0-15 | 0.1-3 |
| Emulsifier | 0-10 | 1.2-8 |
| VOCs in total | <5% | <2% |

*exclusive of surfactant loading in microemulsion, if present

The inventive composition includes a non-ionic surfactant illustratively including fatty alcohols, polyoxypropylene glycol alkyl ethers, glycerol alkyl esters, and the like; an anionic surfactant illustratively including an alkyl sulfate, alkyl benzene sulfonate, alkyl ether phosphate, alkyl carboxylates, and the like; or a combination thereof. Preferably, a non-ionic surfactant is $C_{12}$-$C_{15}$ alkyl ethoxylated alcohol having an average degree of ethoxylation of from 3 to 7.

The inventive composition includes of a solvent of the formula $R^1$—C(O)N(CH$_3$)$_2$, a dibasic ester microemulsion or a combination thereof. In $R^1$—C(O)N(CH$_3$)$_2$ where $R^1$ is a $C_2$-$C_{20}$ alkane, $C_3$-$C_{20}$ alkene, $C_6$-$C_{20}$ diene, or $R^2$—C(O)O—(CH$_2$)$_n$ where $R^2$ is a $C_1$-$C_{20}$ alkane, $C_3$-$C_{20}$ alkene, or $C_6$-$C_{20}$ diene, and n is an integer of between 1 and 10. Commercially available embodiments of $R^1$—C(O)N(CH$_3$)$_n$ illustratively include N,N-dimethyl 9-decenamide, and N,N-dimethyl 3-decenamide. $R^1$—C(O)N(CH$_3$)$_n$ is present at a total weight percent present from 0.1 to 10 percent and preferably present from 1 to 4 total weight percent. In still other embodiments, $R^1$—C(O)N(CH$_3$)$_2$ is present from 1.7 to 3.8 total weight percent. The solvent $R^1$—C(O)N(CH$_3$)$_2$ is used in an inventive composition alone, or in combination with a microemulsion.

A dibasic ester microemulsion is preferably premixed and provided as a concentrate that is intermixed with the remaining composition constituents. Representative dibasic esters for an inventive microemulsion component are dimethyl-2-methyl glutarate, diesters of succinates, glutarates, and adipates, or a combination thereof. A preferred dibasic ester microemulsion operative herein includes an anionic surfactant that is water soluble and non-soaping and includes an organic hydrophobic group containing between 8 and 26 carbon atoms and preferably between 8 and 20 aliphatic carbons along with at least one hydrophilic moiety of hydroxyl, sulfonate, sulfate, or carboxylate. Hydrophobic portion of molecule typically includes a $C_8$-$C_{22}$ alkyl, aryl, or acyl group. The surfactants are present as salts along with salt forming cation common to the art, such as sodium, potassium, or ammonia. Non-soaping anionic surfactants operative herein illustratively include linear alkyl benzene sulfonates, olefin sulfonates, hydroxyl alkane sulfonates, paraffin sulfonates, ethoxylated $C_8$-$C_{24}$ alkyl ether sulfates, and di($C_1$-$C_8$ alkyl) sulfosuccinates, and combinations thereof. In addition to the non-soaping water soluble anionic surfactant, the dibasic ester microemulsion component of an inventive composition is intermixed with a polar organic molecule, the polar organic molecule having a hydrophobic aliphatic portion and at least one hydrophilic moiety. The anionic surfactant is typically present at 10 to 40 weight percent of the dibasic ester microemulsion. Typically, the molecular weight of a polar organic component of a microemulsion is between 50 and 500 atomic mass units. It is also appreciated that molecular emulsifiers as detailed above are also operative herein as the polar organic component of a microemulsion component. In addition to the molecular emulsifiers, a polar organic component operative in an inventive composition illustratively includes $C_2$-$C_{14}$ diols; glycols such as neopentyl glycol; dibasic esters such as $C_1$-$C_6$ esters of adipic, glutaric and succinic acids; glycol ethers; and combinations thereof. The polar organic component is typically present at 50 to 75 weight percent of the microemulsion. Dibasic esters represent a preferred class of microemulsion solvents. Preferably, the non-soaping anionic surfactant is intermixed with at least two different types of polar organics in the presence of a majority phase water to form a microemulsion. Representative formulations and techniques for formation of microemulsions are illustratively detailed in U.S. Pat. No. 5,523,025 and U.S. Pat. No. 6,165,962. Optionally, terpenes or terpenoids are added to the dibasic ester microemulsion to facilitate soil and lipophilic resin or debris removal. Terpenes and terpenoids suitable for inclusion in a dibasic ester microemulsion illustratively include limonene, and turpentine spirits. An inventive dibasic ester microemulsion component is readily formed by mixing together: between 20-60 microemulsion total weight percent polar organics, 20-60 microemulsion total weight percent water, 10-40 percent anionic surfactant, and optionally, between 0-20 percent terpene/terpenoids. Preferably, the dibasic ester microemulsion constituents are chosen to afford a polar bonding value of between 2 and 3.3 along with a simultaneous hydrogen bonding value of between 4.5 and 6, as determined by Hansen solubility parameters, using the Y-MB method. A dibasic ester microemulsion is present at a total weight percent of between 0.1 and 10 percent and preferably between 1 and 4 total weight percent. In still other embodiments, the dibasic ester microemulsion is present from 1.7 to 3.8 total weight percent. When both solvents of $R^1$—C(O)N(CH$_3$)$_2$ and the dibasic ester micioemulsion are present, the total weight percent of solvent is present from 0.2 to 15 percent and preferably present from 1 to 5 total weight percent. Typical ratios of the solvents of $R^1$—C(O)N(CH$_3$)$_2$ to dibasic ester micioemulsion are from 0.1-10:1.

A co-solvent is provided that surprisingly enhances the range and efficacy of the inventive composition alone or when impregnated into a wipe to remove various types of stains and debris coatings. The co-solvent is $C_4$-$C_{28}$ acid ester, $C_9$-$C_{16}$ hydrocarbons having a boiling in the range of 150° C. to 290° C., butyl 3-hydroxybutyrate, or a combination thereof. The co-solvent is present from 0.1 to 10 total weight percent and preferably between 1 and 4 total weight percent. Typical ratios of co-solvent to solvent are from 0.1-1:1.

An inventive composition also includes an emollient. An emollient operative herein illustratively includes hydrophobic organo-silicone-based polymers with repeating siloxane (Si—O) units and include linear, cyclic and cross-linked varieties of cyclomethicones, dimethicones, phenyl-modified silicones, alkyl-modified silicones, silicone resins, and combinations thereof; unsaturated esters or fatty esters, such as ethyl-, hexyl-stearate, isopropyl myristate, caprylic/capric triglycerides; polyols; glycerol; glycerine; cetyl alcohol; carbopol; ethoxylated castor oil; paraffin oils; lanolin; alkylene glycol or polymer formed thereof; mineral oil; wheat germ extract; jojaba extract; and combinations thereof. An alkylene glycol operative herein is ethylene glycol, propylene glycol, polyethylene glycol, polypropylene glycol, a mixed poly(ethylene glycolpropylene glycol), and a combination thereof. Typical quantities of an emollient present in the inventive composition range from 0.1-10 total weight percent with 1-6 total weight percent being preferred.

An inventive composition optionally includes one or more emulsifiers to promote phase homogeneity and storage stability of the inventive composition. It is appreciated that the emulsifiers also can facilitate the solubilization of a target soil, resin, or other substance disintegration into a soluble or colloidal form within an inventive composition. Emulsifiers operative herein are operatively limited only in being chemically-compatible and substantially nonreactive with other components of an inventive composition, and in quantities required to retain pH storage stability and phase homogeneity. Types of emulsifiers operative herein include $C_6$-$C_{12}$ alcohol ethoxide-propoxide adducts, polymeric carboxylates, and molecular emulsifiers. It is appreciated that the overall loadings of emulsifiers of the present invention and combinations thereof are somewhat variable based on specific identities; however, factors relevant in selecting the quantity of emulsifiers include quantity of microemulsion present, composition viscosity, and solvent amount and properties. Molecular emulsifiers characterized by a molecular weight of generally less than about 500 atomic mass units include aliphatic sequences as well as hydrophilic substituents such as one or more of the moieties of hydroxyl, carboxylate, quaternary amine, and sulfonate. A molecular emulsifier operative herein illustratively includes triethanolamine, cetyl stearyl alcohol, sorbitan sesquioleate, polyoxyethylene sorbitan monopalmitate, polyoxyethylene sorbitan mono-oleate, non-ethoxylated glyceryl monostearate, cetearyl alcohol, sodium stearoyl lactylate, lecithin, and combinations thereof. Typically, a molecular emulsifier is present from 0 to 10 total weight percent with 1.2-8 total weight percent being preferred.

Optional additives to a base inventive composition that are well suited for the formation of a liquid hand cleaning composition include: fragrance compounds that are optionally present from 0.001 to 3 total percent; polyvalent metal ion salts such as magnesium oxide, magnesium sulfate, magnesium hydroxide, magnesium chloride, magnesium carboxylates, magnesium halides, magnesium nitrates, as well as aluminum, iron, calcium, and other polyvalent metal ions forming salts with these anions, the polyvalent metal ion salts are optionally present from 0 to 2 total weight percent and are well suited for improving lipophilic soil lift in water containing higher salt loadings; an antimicrobial to improve storage stability illustratively includes quaterniums, triclosan, PCMX, and other conventional antibacterials, an antimicrobial is optionally present from 0 to 2 total weight percent and preferably. between 0.005 and 1 total weight percent; a foaming agent is optionally present from 0 to 2 total weight percent and preferably, between 0.2 and 0.6 total weight percent; dibasic esters are typically present between 0 and less than 0.4 total weight percent and preferably, present at less than 0.2 total weight percent; a colorant is optionally present in an amount of from 0 to 1 total weight percent and preferably, from 0 to 0.3 total weight percent; and a pH modifying source of a mineral acid, organic acid, or hydroxide source such as sodium hydroxide or potassium hydroxide is optionally present in a quantity appropriate to adjust overall inventive composition pH to a desired value while preserving pH storage stability and phase stability thereof. An inventive composition typically has pH values range from 6 to 9 fully formulated.

Preferably, the inventive composition is impregnated or even saturated into a towel preferably when the towel is hydrophobic. It is appreciated that frictional forces applied between a towel surface even if lacking an abrasive and a target surface to be cleaned is sufficient to promote soil removal or a soil film therefrom. More preferably, the towel has an abrasive adhered to at least one of the opposing surfaces thereof. A plurality of abrasive towels are readily provided in a continuous, perforated, rolled cylinder of towels or as a stack of such towels. The line of perforation presents a line of weakness by which the towels can be easily separated. The towels are inserted on-end into a selectively resealable, preferably cylindrical container, with the axis of the cylinder being aligned in an essentially vertical orientation. The inventive composition is then added to the container, preferably by pouring the same over the cylinder of towels, thereby moistening the towels with the inventive cleaning composition within the container. The capillary action associated with the void volume of the towel as discussed above causes the inventive cleaning formulation to be evenly distributed throughout the cylinder of towels.

An example of a suitable container for holding the towels is an essentially airtight lid on a cylindrical or hexahedral rectilinear container defining an interior volume, the lid can be selectively sealed, the lid having a hinged cap. The opening of the cap allows for the passage of towels from the interior of the sealed container via the opening, so individual towels can be removed from the interior container by pulling the towel and tearing the same off of the towel roll at the perforated line located between each individual towel. The opening is appropriately sized to allow for the removal of excess liquid from each individual towel as it is removed from the container. Alternatively towels are accordion folded and stacked in a hexahedral container and the top towel drawn through the lid.

In use, an individual towel is removed from the container as described above. When properly prepared, the towel contains an amount of cleanser sufficient to thoroughly cleanse the skin of the user. As the towel is rubbed on the skin, it releases the liquid cleaner and allows it to have extended contact time with the skin, and also provides for continuous cleaning without the need to apply additional cleaner. The abrasive character of the towel facilitates removal of embedded soils without leaving any abrasive residue on the skin. Residue would otherwise necessitate rinsing the skin with water after the cleansing process to thoroughly remove such abrasive residue. However, it is appreciated that an abrasive free and an inventive composition suspended are operative to clean a target surface. Thus, a waterless hand cleaner article is provided without the negative features associated with the conventional waterless hand cleaners of the prior art.

The inventive composition also assures efficient use of the cleaner, as the proper amount of cleaner is provided for each individual use. Other low viscosity liquid cleaners tend to be wasted as the low viscosity associated with such cleaners often causes them to run off of the skin. Gelatinous cleaners are also difficult to use efficiently, as the user often utilizes too little, thereby necessitating a repeated application; or too much, requiring a cloth or towel to remove the wasted excess.

Furthermore, the towel of the present invention acts not only as a medium for the cleaning formulation and as a vehicle for the abrasive ingredient, but it also serves to dry the skin after the cleanser has been used and has partially evaporated from the towel.

The present invention is further detailed with respect to the following nonlimiting examples. Unless otherwise specified, the percentages detailed herein are total weight percent of the inventive formulation.

COMPARATIVE EXAMPLE A

To 500 milliliters of municipal water is added sequentially 27 grams of $C_{12}$-$C_{15}$ non-ionic surfactant with 7 moles ethylene oxide (EO), 25.8 grams of a microemulsion is then added, the microemulsion being composed of 20 emulsion percent sodium di(hexyl)sulfosuccinate, 40 percent dibasic esters, and 10 microemulsion weight percent of polyethylene glycol (MW 200). With addition of the microemulsion, additional components are added including 15 grams of ISOPAR M (hydrocarbon solvent); 5 grams of butyl hydroxytoluene (BHT); 3 grams of propylene glycol; 3 grams isopropyl myristate; 2.5 grams fragrance; 4 grams of vegetable oil; and 1 gram each of lanolin, aloe vera, vitamin E oil, and jojoba oil. The volume is brought to approximately 1 liter with the addition of more municipal water and the mixture is stirred at 20° Celsius until homogeneous. This composition is detailed in U.S. Pat. No. 8,809,255 as an effective cleaning composition and used herein as a positive control.

EXAMPLE 1

The cleaning composition of Comparative Example A is reformulated with 10 grams of N,N-dimethyl 9-decenamide composition in lieu of the microemulsion detailed above in Comparative Example A with the quantity of water being adjusted to compensate for the differential in the amount of active components.

COMPARATIVE EXAMPLE B

The cleaning composition of Comparative Example A is reformulated with 10 grams of 9-decenoic acid methyl ester in lieu of the microemulsion detailed above in Comparative Example 1 with the quantity of water being adjusted to compensate for the differential in the amount of active components.

COMPARATIVE EXAMPLE C

The cleaning composition of Comparative Example A is reformulated with 10 grams of 9-dodecenoic acid methyl ester and 7.7 grams of diethylhexyl sodium sulfosuccinate in lieu of the microemulsion detailed above in Comparative Example A with the quantity of water being adjusted to compensate for the differential in the amount of active components.

COMPARATIVE EXAMPLE D

The cleaning composition of Comparative Example A is reformulated with 10 grams of 9-dodecenoic acid methyl ester and 12.97 grams of dibasic ester blend (DBE-2) in lieu of the microemulsion detailed above in Comparative Example 1 with the quantity of water being adjusted to compensate for the differential in the amount of active components.

COMPARATIVE EXAMPLE E

The cleaning composition of Comparative Example A is reformulated with 10 grams of 9-dodecenoic acid methyl ester and 5.2 grams of neopentyl glycol in lieu of the microemulsion detailed above in Comparative Example 1 with the quantity of water being adjusted to compensate for the differential in the amount of active components.

COMPARATIVE EXAMPLE F

The cleaning composition of Comparative Example A is reformulated with 10 grams of 9-dodecenoic acid methyl ester and 7.7 grams of diethylhexyl sodium sulfosuccinate and 5.2 grams of neopentyl glycol in lieu of the microemulsion detailed above in Comparative Example 1 with the quantity of water being adjusted to compensate for differential in other components.

Testing

Coupons of aluminum are soiled with various substances targeted for removal and scrubbed with various wipes. In cases where the soil is not fully removed after 500 cycles, the panels were visually compared to rank the wipe's cleaning efficiency. The compositions are saturated into commercially available, dual-textured meltblown polypropylene wipes and allowed to rest for 2 days prior to usage. The test mechanism utilizes a modified BYK abrasion tester. The wipes are mounted to a plastic block with spring tension mechanism to keep the wipe on the block. The block is placed within a sled such that the wipe surface faces down while the opposing test panel resides below the sled path facing upwards. The block is pressed against the test surface with a total weight of approximately 3 lb (combination of block weight, sled weight, and 1 lb of added weight attached to sled). A counter is built into the testing mechanism that increases by one unit for every back & forth cycle of the sled.

The soils used included:

DYKEM® Steel Blue paint. A quart of steel blue paint emptied into an open container which permitted the test coupons to be dipped for an even coating. The panels are then dried at room temperature and cured for ~48 h before testing.

Permanent Marker. A Sanford Magnum 44 broad tip permanent marker is utilized to make two passes vertically down the center of the test coupon. The coupon is allowed to dry at room temperature and cure for ~48 h before testing.

Spray Paint. RUST-OLEUM® PAINTER'S TOUCH® Enamel paint is applied to give as uniform coat as possible across the set of test coupons. These are allowed to dry/cure for ~48 hours at room temperature prior to testing.

Asphaltic Coating. PERMATEX® Under-Coating #80072 is applied to give as uniform a coating as possible across the set of test coupons. These are allowed to dry/cure for ~48 hours at room temperature prior to testing.

The results are summarized in Table 2. Where partial removal after 500 cycles is noted, the samples are ranked based on visual appearance of coupons with Roman numerals with one being best.

TABLE 2

Test results for Example 1 and Comparative Examples A-F

| | Steel Blue Swipes for removal | Marker Swipes for removal | Spray Paint Swipes for removal | Asphaltic Swipes for removal |
|---|---|---|---|---|
| Comparative Ex. A (positive control) | 80 | Partial (I) | Partial (II) | Partial (I) |
| Example 1 | 40 | 30 | Partial (I) | 300 |
| Comparative Ex. B | 90 | Partial (II) | Partial (V) | 480 |
| Comparative Ex. C | 100 | Partial (VI) | Partial (IV) | Partial (IV) |
| Comparative Ex. D | 50 | Partial (III) | Partial (III) | Partial (III) |
| Comparative Ex. E | 160 | Partial (IV) | Partial (VI) | Partial (V) |
| Comparative Ex. F | 150 | Partial (V) | Partial (VII) | Partial (II) |

EXAMPLE 2

The cleaning composition of Comparative Example A is reformulated with the addition of 10 grams of microalgae fatty acid methyl ester to Comparative Example A with the quantity of water being reduced to compensate for the addition.

EXAMPLE 3

The cleaning composition of Comparative Example A is reformulated with the addition of 10 grams of butyl 3-hydroxybutyrate to Comparative Example A with the quantity of water being reduced to compensate for the addition.

EXAMPLE 4

The cleaning composition of Comparative Example A is reformulated with the addition of 10 grams of 9-dodecenoic acid methyl ester to Comparative Example A with the quantity of water being reduced to compensate for the addition.

COMPARATIVE EXAMPLE G 2.5 grams of $C_{12}$-$C_{15}$ non-ionic surfactant with 7 moles ethylene oxide (EO) per liter water is used as a negative control to address the mechanical contribution to cleaning.

Testing

The compositions of Examples 2-4 and Comparative Example G are saturated into wipes and tested on coupons as detailed above.

The results are summarized in Table 3. Where partial removal after 500 swipes is noted, the samples are ranked based on visual appearance of coupons with Roman numerals with one being most effective. Comparative Example A results are reproduced for context.

TABLE 3

Test results for Examples 2-4 and Comparative Examples A and G.

| | Steel Blue Swipes for removal | Marker Swipes for removal | Spray Paint Swipes for removal | Asphaltic Swipes for removal |
|---|---|---|---|---|
| Comparative Ex. A (positive control) | 80 | Partial (III) | Partial (IV) | Partial (I) |
| Example 2 | 50 | Partial (I) | Partial (III) | 240 |
| Example 3 | 40 | Partial (II) | Partial (II) | 330 |
| Example 4 | 50 | 450 | Partial (I) | 170 |
| Comparative Ex. G (negative control) | 230 | Partial (V) | No effect | Partial (II) |

Patent documents and publications mentioned in the specification are indicative of the levels of those skilled in the art to which the invention pertains. These documents and publications are incorporated herein by reference to the same extent as if each individual document or publication was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

The invention claimed is:

1. A hand cleaning article comprising:
   A) a towel presenting two opposed surfaces; and
   B) a hand cleaning composition impregnated into said towel, said composition comprising:
      a) 0.5 to 15 total weight percent of a first non-ionic surfactant that is a C12-C15 alkyl ethoxylated alcohol having an average degree of ethoxylation of from 3 to 7;
      b) 0.1 to 10 total weight percent of a solvent selected from the group consisting of:
         1) a dibasic ester microemulsion;
         2) a compound having the formula $R^1$—C(O)N(CH$_3$)$_2$ where $R^1$ is a C2-C20 alkane, C3-C20 alkene, or C6-C20 diene;
         3) a compound having the formula $R^2$—C(O)O—(CH$_2$)$_n$ where $R^2$ is a C1-C20 alkane, C3-C20 alkene, or C6-C20 diene, and n is an integer of between 1 and 10, or a combination of any of the aforementioned;
      c) 0.1 to 15 total weight percent of an organic co-solvent selected from the group consisting of:
         i) a 9-decanoic acid methyl ester;
         ii) C9-C16 hydrocarbons having a boiling point in the range of 150° C. to 290° C.;
         iii) butyl 3-hydroxybutyrate; and
         iv) an additional C4-C28 add ester, or a combination thereof, with the proviso that at least the 9-decanoic add methyl ester must be present; and
      d) water present as a majority by total weight percent of the composition.

2. The hand cleaning article of claim 1 wherein said C$_9$-C$_{16}$ hydrocarbons is present and comprises hydrotreated hydrocarbons.

3. The hand cleaning article of claim 1 further comprising a second non-ionic surfactant, an anionic surfactant, or a combination thereof.

4. The hand cleaning article of claim 1 further comprising 0.1 to 10 total weight percent of at least one emollient.

5. The hand cleaning article of claim 1, wherein the VOC content of the composition is less than 2 total weight percent.

6. The hand cleaning article of claim 1 wherein said dibasic ester microemulsion is present.

7. The hand cleaning article of claim 6 wherein said microemuision is premixed and provided as a concentrate to the composition in a total amount of from 1 to 4 total weight percent, said microemuision including an anionic surfactant.

8. The hand cleaning article of claim 7 wherein said microemulsion anionic surfactant is a sulfosuccinate.

9. The hand cleaning article of claim 7 wherein said microemuision is present and said compound having the formula $R^1$—C(O)N(CH$_3$)$_2$ is not present.

10. The hand cleaning article of claim 1 where $R^1$—C(O)N(CH$_3$)$_2$ is present as N,N-dimethyl 9-decenamide.

11. The hand cleaning article of claim 10 wherein said N,N-dimethyl 9-decenamide is present in a total amount of from 1 to 4 total weight percent.

12. The hand cleaning article of claim 11 wherein said N,N-dimethyl 9-decenamide is present and said dibasic ester microemulsion is not present.

13. The hand cleaning article of claim 1 further comprising at least one additive of a pH adjusting material, an antioxidant, a fragrance, a dye, and a foaming agent.

14. The hand cleaning article of claim 1 further comprising a fungicide.

15. The hand cleaning article of claim 14 wherein said fungicide is present from 0.1 to 10 total weight percent.

16. The hand cleaning article of claim 1 further comprising a polyvalent metal ion salt.

17. The hand cleaning article of claim 1 further comprising an abrasive ingredient adhered to at least one of the two opposed surfaces.

18. The article of claim 17 further comprising:
   a plurality of said towels being provided in a continuous rolled cylinder, each of said plurality of said towels separated at a line of perforation; and
   a selectively sealable, evaporation resistant container having a hollow interior in which said plurality of said towels are housed, the axis of said cylinder being aligned in an essentially vertical orientation within said container, and a lid associated therewith, said lid defining an opening therein for receiving said plurality of said towels therethrough, the opening having a selectively closeable cap associated therewith.

19. A method for preparing a hand cleaning article, said method comprising:
   providing a plurality of towels in a continuous rolled cylinder separated by a line of perforation, said towels presenting two opposed surfaces, and having an abrasive ingredient adhered to at least one of the two opposed surfaces, said towel being capable of absorbing and retaining fluid while maintaining its abrasive quality;

placing said plurality of towels in a selectively sealable container having a hollow interior in which said plurality of towels form a cylinder, said container having a lid with an opening therein, and a selectively closable cap associated therewith; and impregnating said plurality of towels with a predetermined amount of the hand cleaning composition of present claim 1, and sealing said lid on said container.

20. A hand cleaning article comprising:
A) a towel presenting two opposed surfaces; and
B) a hand cleaning composition impregnated into said towel, said composition comprising:
 a) 0.5 to 15 total weight percent of a first non-ionic surfactant that is a C12-C15 alkyl ethoxylated alcohol having an average degree of ethoxylation of from 3 to 7;
 b) 0.1 to 10 total weight percent of a solvent which is a compound having the formula $R^1$—$C(O)N(CH_3)_2$ present as N,N-dimethyl 9-decenamide, alone or in combination with a dibasic ester microemuision;
 c) 0.1 to 15 total weight percent of an organic co-solvent selected from the group consisting of:
  i) a 9-decanoic acid methyl ester;
  ii) C9-C16 hydrocarbons having a boiling point in the range of 150° C. to 290° C.;
  iii) butyl 3-hydroxybutyrate; and
  iv) an additional C4-C28 acid ester, or a combination thereof, with the proviso that at least the 9-decanoic add methyl ester must be present; and
 d) water present as a majority by total weight percent of the composition.

\* \* \* \* \*